United States Patent [19]

Maxwell

[11] 4,452,798

[45] Jun. 5, 1984

[54] 1-SUBSTITUTED PHENYL-4-ALKYL HYDANTOIN PIPERAZINE COMPOUNDS AS ANTIHYPERTENSIVE AGENTS

[75] Inventor: Donald R. Maxwell, Pinckney, Mich.

[73] Assignee: Warner-Lambert Company, Morris Plains, N.J.

[21] Appl. No.: 391,198

[22] Filed: Jun. 22, 1982

[51] Int. Cl.³ ............... C07D 403/08; A61K 31/495
[52] U.S. Cl. .................... 424/250; 544/358; 544/370; 548/308
[58] Field of Search ............ 544/370; 424/250

[56] References Cited

U.S. PATENT DOCUMENTS

| | | | |
|---|---|---|---|
| 2,836,595 | 5/1958 | Parcell | 544/392 |
| 3,037,024 | 5/1962 | Parcell | 544/392 |
| 3,494,932 | 2/1970 | Brabander | 544/370 |
| 3,806,510 | 4/1974 | Parcell | 544/392 |
| 3,879,395 | 4/1975 | Nordin | 544/392 |
| 3,892,748 | 7/1975 | Hayao et al. | 544/370 |
| 4,038,279 | 7/1977 | Renth et al. | 544/392 |

FOREIGN PATENT DOCUMENTS

| | | | |
|---|---|---|---|
| 2638184 | 3/1977 | Fed. Rep. of Germany | 424/250 |
| 1368256 | 9/1974 | United Kingdom | 424/250 |

*Primary Examiner*—Donald G. Daus
*Assistant Examiner*—S. A. Gibson
*Attorney, Agent, or Firm*—Jerry F. Janssen

[57] ABSTRACT

Certain substituted phenylpiperazine compounds useful as antihypertensive agents are described. Methods for their preparation and use are disclosed.

7 Claims, No Drawings

1-SUBSTITUTED PHENYL-4-ALKYL HYDANTOIN PIPERAZINE COMPOUNDS AS ANTIHYPERTENSIVE AGENTS

BACKGROUND OF THE INVENTION

U.S. Pat. No. 3,806,510 discloses certain 4-(2-alkylthiophenyl)piperazin-1-yl hydantoin compounds which are central nervous system depressants.

U.S. Pat. No. 3,879,395 discloses certain 4-(2-alkylthiophenyl)-1-piperazinylalkylamino-5,5-dimethyl-2-cyclohexen-1-ones which are central nervous system depressants.

West German Pat. No. 26 38 184 describes the N-oxide of 1-[3-(5,5-dimethyl-3-oxocyclohexen-1-ylamino)propyl]-4-(2-methoxyphenyl)piperazine.

SUMMARY OF THE INVENTION

The invention sought to be patented in its generic chemical compound aspect is a compound having the structural formula I

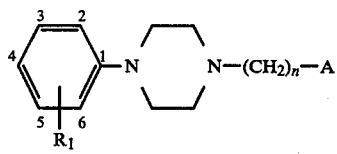

wherein A is

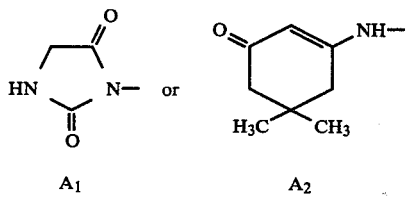

$A_1$    $A_2$ n is 2, 3, or 4; $R_1$ is hydrogen, alkyl of from one to six carbon atoms or alkoxy of from one to six carbon atoms; and the pharmaceutically acceptable salts thereof; provided that when A is $A_1$ and n is 3, $R_1$ is not 3-OCH$_3$, and when A is $A_2$ and n is 3, $R_1$ is not 2-OCH$_3$ or 4-OCH$_3$ and when A is $A_2$ and n is 4 $R_1$ is not 4-CH$_3$ or 4-OCH$_3$.

The invention sought to be patented in a first subgeneric aspect of its chemical compound aspect is a compound having the structural formula

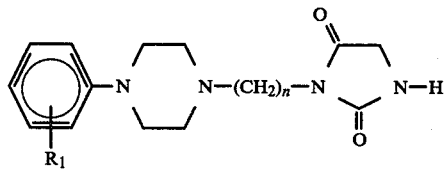

wherein n is 2, 3, or 4; $R_1$ is hydrogen alkyl of from one to six carbon atoms or alkoxy of from one to six carbon atoms; and the pharmaceutically acceptable salts thereof;

provided that when n is 3, $R_1$ is not 3-OCH$_3$.

The invention sought to be patented in a second subgeneric aspect of its chemical compound aspect is a compound having the structural formula

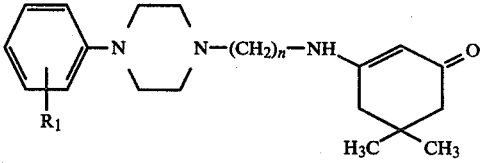

wherein n is 2, 3, or 4; $R_1$ is hydrogen, alkyl of from one to six carbon atoms, or alkoxy of from one to six carbon atoms; and the pharmaceutically acceptable salts thereof;

provided that when n is 3, $R_1$ is not 2-OCH$_3$ or 4-OCH$_3$ and when n is 4, $R_1$ is not 4-CH$_3$ or 4-OCH$_3$.

The invention sought to be patented in a third subgeneric aspect of its chemical compound aspect is a compound having the structural formula I wherein $R_1$ is located at either the 3- or 4-position of the benzene ring; and the pharmaceutically acceptable salt thereof; provided that when A is $A_1$ and n is 3, $R_1$ is not 3-OCH$_3$ and when A is $A_2$ and n is 3, $R_1$ is not 4-OCH$_3$ and when n is 4, $R_1$ is not 4-CH$_3$ or 4-OCH$_3$.

The invention sought to be patented as species of the chemical compound aspect of the invention are the compounds having the names:

3-[4-[4-(3-methylphenyl)-1-piperazinyl]butyl]hydantoin;

3-[4-[4-(4-methylphenyl)-1-piperazinyl]butyl]hydantoin;

5,5-dimethyl[3-[[4-(3-ethoxyphenyl)-1-piperazinyl]butyl]amino]-2-cyclohexen-1-one;

and the pharmaceutically acceptable salts thereof.

The invention sought to be patented in its pharmaceutical composition aspect is a composition useful for treating hypertension in a mammal consisting essentially of a compound having the structural formula I or mixtures thereof in combination with a pharmaceutically acceptable carrier.

The invention sought to be patented in its pharmaceutical method aspect is a method for treating hypertension in a mammal in need of such treatment; which comprises administering an antihypertensive effective amount of the above defined pharmaceutical composition to said mammal.

DESCRIPTION OF THE PREFERRED EMBODIMENTS

The compounds of the invention are readily prepared by procedures well known in the art.

Thus, the compounds of the invention having structural formula I wherein A is $A_1$

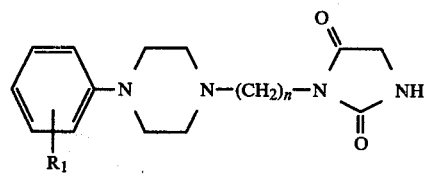

may be prepared by heating a correspondingly substituted, disubstituted urea compound of the formula II

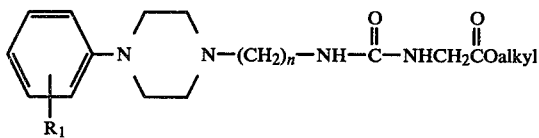

or a salt thereof in the presence of a ring closure agent. This ring closure may be performed by well known procedures for example as described in U.S. Pat. No. 3,806,510. The relevant teachings of this patent are incorporated herein by reference. In the above formula II $R_1$ and n are as previously defined and the term "alkyl" is defined as any convenient alkyl group, preferably by from one to six carbon atoms and most preferably methyl or ethyl.

The compounds of the invention having structural formula I wherein A is $A_2$

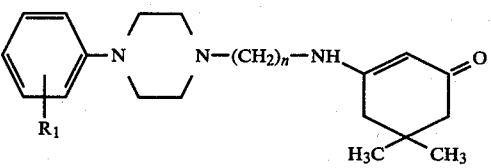

may be prepared by condensing a correspondingly substituted 4-($R_1$-substitutedphenyl)-1-piperazinylalkylamine having the structural formula III

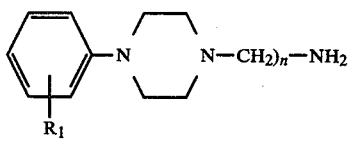

with 5,5-dimethyl-1,3-cyclohexanedione, which compound is known as dimedone. This condensation may be performed by well known procedures for example as described in U.S. Pat. No. 3,879,395. The relevant teachings of this patent are incorporated herein by reference. In the above formula III $R_1$ and n are as previously defined.

The above described starting materials II and III may be readily prepared by procedures known in the art. See for example U.S. Pat. Nos. 3,879,395; 3,806,510; and 2,836,595.

The compounds of the invention are new chemical substances which are useful pharmaceutical agents for the treatment of hypertension. The antihypertensive effects of representative compounds of the invention was established by the following standard procedure.

Spontaneously hypertensive male rats (Charles River, Wilmington) weighing between 325–395 grams were cannulated for directly monitoring arterial blood pressure and heart rates. Three or four rats were orally dosed with each test compound dissolved/suspended in 4% gum acacia. The rats received 10 mg/kg body weight of test compound and were continuously monitored for blood pressure and heart rate changes for up to 24 hours postdrug. If blood pressure fell in at least two of the rats tested by at least 10% for at least two consecutive hours (4–30 minute periods), that compound was considered "active" in this test.

Representative compounds of the invention gave the following results when tested by the above-identified procedure.

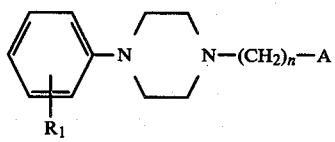

| $R_1$ | n | A | % Δ bp at one hour |
|---|---|---|---|
| H | 3 | $A_1$ | −22 |
| 2-$CH_3$ | 4 | $A_1$ | −41 |
| 3-$CH_3$ | 4 | $A_1$ | −48 |
| 4-$CH_3$ | 4 | $A_1$ | −34 |
| 2-$OCH_3$ | 2 | $A_1$ | −33 |
| 2-$OCH_3$ | 3 | $A_1$ | −37 |
| 2-$OCH_3$ | 4 | $A_1$ | −19 |
| 3-$OC_2H_5$ | 4 | $A_1$ | −18 |
| H | 3 | $A_2$ | −29 |
| 2-$CH_3$ | 4 | $A_2$ | −19 |
| 3-$CH_3$ | 3 | $A_2$ | −12 |
| 3-$CH_3$ | 4 | $A_2$ | −27 |
| 2-$OCH_3$ | 4 | $A_2$ | −41 |
| 3-$OCH_3$ | 3 | $A_2$ | −15 |
| 3-$OC_2H_5$ | 4 | $A_2$ | −27 |

The compounds of the invention form pharmaceutically acceptable salts with organic and inorganic acids. Examples of suitable acids for salt formation are hydrochloric, sulfuric, phosphoric, acetic, citric, oxalic, malonic, salicyclic, malic, fumaric, succinic, ascorbic, maleic, methanesulfonic, and the like. The salts are prepared by contacting the free base form with a sufficient amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl and alkoxy groups contemplated by the invention comprise both straight and branched carbon chains of from one to about six carbon atoms. Representative of such groups are methyl, ethyl, isopropyl, pentyl, 3-methylpentyl, methoxy, ethoxy, 2-propoxy, 3-methylpentoxy, and the like. Preferred are methyl, ethyl, methoxy, and ethoxy.

The compounds of the invention comprise an unbranched alkylene chain —$(CH_2)_n$— wherein n is the integer 2, 3, or 4. Preferably, n is the integer 3 or 4.

The compounds of the invention comprise an $R_1$-substitutedphenyl group which substituent, $R_1$, may be located at either the 2-, 3-, or 4-position of the benzene ring. Preferably, $R_1$ is located at the 3- or 4-position of the benzene ring.

The compounds of the invention can be prepared and administered in a wide variety of oral and parenteral dosage forms. It will be obvious to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as antihypertensive agents, the compounds utilized in the pharmaceutical method of this invention are administered at the initial dosage of about 1 mg to about 30 mg per kilogram daily. A daily dose range of about 3 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor's preferred methods for preparing the compounds of the invention.

EXAMPLE 1

3-[4-[4-(3-Methylphenyl)-1-piperazinyl]butyl]hydantoin

To a solution 12.4 g of 1-(4-aminobutyl)-4-(3-methylphenyl)piperazine in 75 ml of toluene is added 7.75 g of ethyl isocyanoacetate. After a mild exothermic reaction has subsided, the solution is heated at 90°–100° C. for 30 minutes. The resulting solution of N-[[4-[4-(3-methylphenyl)-1-piperazinyl]butyl]carbamoyl]glycine, ethyl ester is treated with 110 ml of 20% hydrochloric acid and the mixture is stirred and heated at 90°–100° C. for four hours while the toluene is allowed to evaporate. The remaining mixture is evaporated under reduced pressure, and the residue is dissolved in 200 ml of ethanol-benzene (1:1). The solution is evaporated to dryness under reduced pressure. The residue is dissolved in 100 ml of isopropanol, and the result solution is concentrated by distillation to a volume of approximately 50 ml in order to remove all of the excess water and hydrochloric acid. Ether (150 ml) is added to the concentrate and on cooling 12.7 g of product melting at 166°–170° C. is obtained. Two recrystallizations from isopropanol yields 9.4 g of analytically pure product as the hydrochloride salt; mp 184°–6° C.

EXAMPLE 2

3-[4-[4-(4-Methylphenyl)-1-piperazinyl]butyl]hydantoin

By following the general procedure described in Example 1 10.8 g of 3-[4-[4-(4-methylphenyl)-1-piperazinyl]butyl]hydantoin monohydrochloride melting at 231°–5° C. is obtained from 12.5 g of 1-(4-aminobutyl)-4-(4-methylphenyl)piperazine treated with 7.75 g of ethyl cyanatoacetate in toluene.

EXAMPLE 3

5,5-Dimethyl-3-[[4-(3-ethoxyphenyl)-1-piperazinyl]butyl]amino]-2-cyclohexen-1-one A solution of 13.9 g of 1-(4-aminobutyl)-4-(3-ethoxyphenyl)piperazine and 7.0 g of 5,5-dimethyl-1,3-cyclohexanedione in 80 ml of toluene is heated at reflux with a water separator for four hours, or until one equivalent of water is separated. The solution is treated with charcoal and filtered. Pentane is added to the warm solution until cloudy and on standing 18.1 g of product, mp 115°–117° C. is obtained.

| Calcd for $C_{24}H_{37}N_3O_2$ (399.6): | C, 72.13; | H, 9.33; | N, 10.52 |
|---|---|---|---|
| Found: | C, 72.10; | H, 9.31; | N, 10.42. |

The following compounds were prepared by procedures similar to those described in the examples.

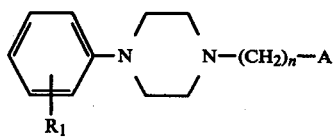

| $R_1$ | n | A | mp | Procedure of Example |
|---|---|---|---|---|
| H | 3 | $A_1$** | 265–268° C. dec | 1 |
| 2-$CH_3$ | 4 | $A_1$* | 232–234° C. | 1 |
| 3-$CH_3$ | 3 | $A_1$* | 233–236° C. dec | 1 |
| 3-$CH_3$ | 4 | $A_1$* | 184–187° C. | 1 |
| 4-$CH_3$ | 4 | $A_1$* | 231–235° C. | 1 |
| 2-$OCH_3$ | 2 | $A_1$* | 240–243° C. | 1 |
| 2-$OCH_3$ | 3 | $A_1$** | 235–238° C. | 1 |
| 2-$OCH_3$ | 4 | $A_1$* | 227–229.5° C. | 1 |
| 3-$OC_2H_5$ | 4 | $A_1$* | 157.5–159° C. | 1 |
| 4-$OCH_3$ | 3 | $A_1$* | 234–236° C. | 1 |
| 2-$OiC_3H_7$ | 4 | $A_1$* | 209–215° C. | 1 |
| H | 3 | $A_2$ | 159–160° C. | 3 |
| 2-$CH_3$ | 4 | $A_2$ | 98–99° C. | 3 |
| 3-$CH_3$ | 3 | $A_2$ | 140–140.5° C. | 3 |
| 3-$CH_3$ | 4 | $A_2$ | 141.5–144° C. | 3 |
| 4-$CH_3$ | 3 | $A_2$ | 182–183° C. | 3 |
| 2-$OCH_3$ | 4 | $A_2$ | 115–117° C. | 3 |
| 3-$OCH_3$ | 3 | $A_2$ | 147–148° C. | 3 |
| 3-$OC_2H_5$ | 4 | $A_2$ | 115–117° C. | 3 |

*hydrochloride salt
**dihydrochloride salt

I claim:
1. A compound having the structural formula

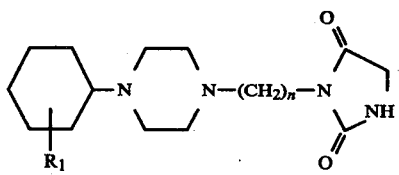

wherein n is 2, 3, or 4; $R_1$ is hydrogen or alkyl of from one to six carbon atoms; and the pharmaceutically acceptable salts thereof.

2. The compounds defined in claim 1 werein n is 4 and the pharmaceutically acceptable salts thereof.

3. The compounds defined in claim 1 wherein $R_1$ is in the 3 or 4 position, and the pharmaceutically acceptable salts thereof.

4. The compound having the name 3-[4-[4-(3-methylphenyl)-1-piperazinyl]butyl]hydantoin, and the pharmaceutically acceptable salts thereof.

5. The compound having the name 3-[4-[4-(4-methylphenyl)-1-piperazinyl]butyl]hydantoin, and the pharmaceutically acceptable salts thereof.

6. A pharmaceutical composition comprising an antihypertensive effective amount of a compound defined in claim 1 in combination with a pharmaceutically acceptable carrier.

7. A method for treating hypertension in a mammal which comprises administering the pharmaceutical composition defined in claim 6 to said mammal.

* * * * *